(12) United States Patent
Hayashi et al.

(10) Patent No.: US 8,398,401 B2
(45) Date of Patent: *Mar. 19, 2013

(54) METHOD FOR MANUFACTURING DENTAL IMPLANT AND DENTAL IMPLANT

(75) Inventors: Junichi Hayashi, Okaya (JP); Michio Ito, Shiojiri (JP)

(73) Assignee: Seiko Epson Corporation, Tokyo (JP)

(*) Notice: Subject to any disclaimer, the term of this patent is extended or adjusted under 35 U.S.C. 154(b) by 263 days.

This patent is subject to a terminal disclaimer.

(21) Appl. No.: 12/179,628

(22) Filed: Jul. 25, 2008

(65) Prior Publication Data

US 2009/0029315 A1 Jan. 29, 2009

(30) Foreign Application Priority Data

Jul. 27, 2007 (JP) .................. 2007-196495

(51) Int. Cl.
*A61C 8/00* (2006.01)

(52) U.S. Cl. .................. 433/173; 433/201.1

(58) Field of Classification Search .......... 433/173–174, 433/201.1, 201.16; 29/896.1; 264/603, 605
See application file for complete search history.

(56) References Cited

U.S. PATENT DOCUMENTS

| | | | | |
|---|---|---|---|---|
| 3,589,011 A | * | 6/1971 | Sneer | 433/174 |
| 3,934,347 A | * | 1/1976 | Lash et al. | 433/173 |
| 4,416,629 A | * | 11/1983 | Mozsary et al. | 433/174 |
| 4,488,875 A | * | 12/1984 | Niznick | 433/173 |
| 4,525,145 A | | 6/1985 | Scheicher et al. | |
| 4,657,510 A | * | 4/1987 | Gittleman | 433/173 |
| 4,713,003 A | * | 12/1987 | Symington et al. | 433/173 |
| 4,713,004 A | * | 12/1987 | Linkow et al. | 433/174 |
| 4,722,688 A | * | 2/1988 | Lonca | 433/173 |
| 4,832,601 A | * | 5/1989 | Linden | 433/173 |
| 4,854,872 A | * | 8/1989 | Detsch | 433/173 |
| 5,033,962 A | | 7/1991 | Scatena | |
| 5,040,982 A | * | 8/1991 | Stefan-Dogar | 433/169 |
| 5,049,073 A | * | 9/1991 | Lauks | 433/173 |
| 5,071,350 A | * | 12/1991 | Niznick | 433/173 |
| 5,087,199 A | * | 2/1992 | Lazarof | 433/173 |
| 5,116,225 A | * | 5/1992 | Riera | 433/173 |

(Continued)

FOREIGN PATENT DOCUMENTS

| | | |
|---|---|---|
| DE | 4021813 | 1/1992 |
| DE | 4230009 | 4/1993 |

(Continued)

OTHER PUBLICATIONS

JP Office Action 2009-099245 dated Oct. 11, 2011.

*Primary Examiner* — Cris L Rodriguez
*Assistant Examiner* — Hao D Mai

(57) ABSTRACT

A dental implant is provided that is capable of reliably preventing elution of metal when the dental implant is applied within an oral cavity and capable of reliably preventing the occurrence of mismatching (bumpy occlusion or the like) when the dental implant is fixed in place. The dental implant includes an abutment comprising a titanium member composed of a body made from titanium or titanium alloy and having a recess, and a ceramic member composed of oxide-based ceramic and having a protrusion fitted within the recess. In a pre-sintered state, the recess has a first surface shape providing a clearance between the recess and the protrusion inserted therein. In a post-sintered state, the recess has a second surface shape corresponding to a surface shape of the protrusion so that the protrusion is in close contact with and fitted to the recess.

6 Claims, 6 Drawing Sheets

U.S. PATENT DOCUMENTS

| | | | |
|---|---|---|---|
| 5,195,891 A * | 3/1993 | Sulc | 433/173 |
| 5,213,500 A * | 5/1993 | Salazar et al. | 433/169 |
| 5,346,396 A | 9/1994 | Hakamatsuka | |
| 5,417,570 A * | 5/1995 | Zuest et al. | 433/177 |
| 5,482,463 A * | 1/1996 | Wilson et al. | 433/173 |
| 5,556,280 A * | 9/1996 | Pelak | 433/172 |
| 5,564,921 A * | 10/1996 | Marlin | 433/172 |
| 5,599,185 A * | 2/1997 | Greenberg | 433/173 |
| 5,678,995 A * | 10/1997 | Kirsch et al. | 433/169 |
| 5,685,714 A | 11/1997 | Beaty et al. | |
| 5,733,122 A | 3/1998 | Gordon | |
| 5,782,918 A * | 7/1998 | Klardie et al. | 606/60 |
| 5,810,590 A * | 9/1998 | Fried et al. | 433/172 |
| 5,871,358 A * | 2/1999 | Ingber et al. | 433/213 |
| 5,888,218 A * | 3/1999 | Folsom | 623/16.11 |
| 5,967,782 A | 10/1999 | Shimodaira et al. | |
| 6,012,923 A * | 1/2000 | Bassett et al. | 433/172 |
| 6,030,219 A * | 2/2000 | Zuest et al. | 433/181 |
| 6,068,478 A * | 5/2000 | Grande et al. | 433/172 |
| 6,244,867 B1 * | 6/2001 | Aravena et al. | 433/172 |
| 6,273,720 B1 * | 8/2001 | Spalten | 433/173 |
| 6,461,160 B1 * | 10/2002 | Sutter | 433/173 |
| 6,644,969 B2 * | 11/2003 | Kumar | 433/173 |
| 6,695,616 B2 * | 2/2004 | Ellison | 433/174 |
| 2001/0037154 A1 | 11/2001 | Martin | |
| 2003/0082499 A1 * | 5/2003 | Halldin et al. | 433/173 |
| 2004/0234926 A1 | 11/2004 | Halldin et al. | |
| 2005/0136378 A1 * | 6/2005 | Ennajimi et al. | 433/173 |
| 2005/0181330 A1 | 8/2005 | Kim et al. | |
| 2006/0014120 A1 | 1/2006 | Sapian | |
| 2010/0062396 A1 | 3/2010 | Hock et al. | |
| 2011/0294090 A1 | 12/2011 | Jung | |

FOREIGN PATENT DOCUMENTS

| | | |
|---|---|---|
| DE | 197 14 759 | 4/1997 |
| DE | 20 2006 001 796 | 2/2006 |
| DE | 10-2005-042091 | 3/2007 |
| EP | 1570804 | 9/2005 |
| EP | 1939153 A1 | 7/2008 |
| JP | 04-049958 | 2/1992 |
| JP | 05-168651 | 7/1993 |
| JP | 5-228161 | 9/1993 |
| JP | 06-048855 | 2/1994 |
| JP | 06-125979 | 5/1994 |
| JP | 08-117247 | 5/1996 |
| JP | 08-117324 | 5/1996 |
| JP | 08-310878 | 11/1996 |
| JP | 10-33562 | 2/1998 |
| JP | 11-071186 | 3/1999 |
| JP | 2000-24004 | 1/2000 |
| JP | 2000-087105 | 3/2000 |
| JP | 2004-313525 | 11/2001 |
| JP | 2003-525685 | 9/2003 |
| JP | 2003-277806 | 10/2003 |
| WO | 01/66022 A1 | 9/2001 |
| WO | 2007-016796 | 2/2007 |

* cited by examiner

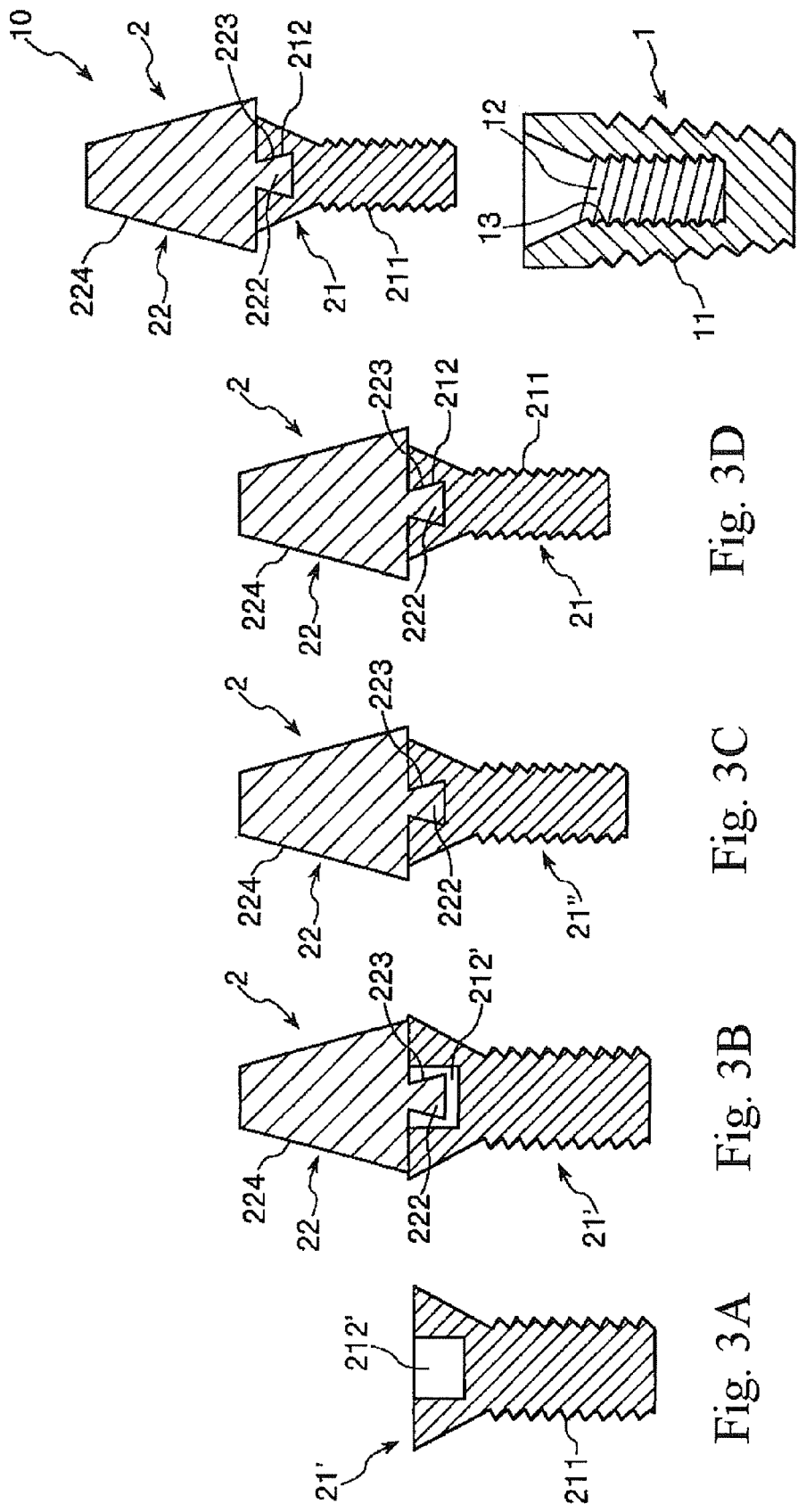

METHOD FOR MANUFACTURING DENTAL IMPLANT AND DENTAL IMPLANT

CROSS-REFERENCE TO RELATED APPLICATION

This application claims a priority to Japanese Patent Application No. 2007-196495 filed on Jul. 27, 2007 which is hereby expressly incorporated by reference herein in its entirety.

BACKGROUND

1. Technical Field

The present invention relates to a method for manufacturing a dental implant and a dental implant manufactured by the method.

2. Related Art

An implant (dental implant) has been extensively used to restore the function of a tooth lost by various causes. In general, the dental implant includes a fixture anchored to a jawbone and an abutment threadedly coupled to the fixture.

A crown restoration is capped on the dental implant (the abutment threadedly coupled to the fixture) and fixed thereto with dental cement, thereby bringing the dental implant into a shape corresponding to that of an original tooth.

Conventionally, from the standpoint of compatibility to a living body, strength and so forth, titanium or titanium alloy has been generally used as a constituent material of the implant (see, e.g., JP-A-2000-24004, page 3, right column, lines 40 to 42).

Ceramic is generally used as a constituent material of the crown restoration to lessen the difference in appearance between the crown restoration and the tooth of a living body.

A metal portion (metal layer) made of gold alloy or the like is arranged on the inner surface (the implant-side surface) of the crown restoration in an effort to improve occlusion or to reliably prevent occurrence of cracks in the crown restoration.

In other words, a laminated body including a metal portion (metal layer) made of metal and a layer made of ceramic is widely used as the crown restoration.

If the crown restoration has the metal portion as set forth above, however, a galvanic cell is formed between the metal portion and the titanium-made implant. This may possibly cause metal to be eluted into the living body, thereby adversely affecting the living body.

With a view to avoid such a problem, it would be conceivable that the metal portion of the crown restoration is fixed to the implant with a relatively large quantity of dental cement so that they should not make contact with each other.

In this case, it becomes difficult to adjust the height and angle of the crown restoration to be fixed to the implant as designed at the outset. It is also difficult to obtain sufficiently high bonding strength.

In order to prevent contact between the titanium or titanium alloy of which the implant is made and the metal portion of the crown restoration, it would also be conceivable that the titanium or titanium alloy is coated with insulating ceramic.

Ceramic is usually inferior in its bondability with titanium or titanium alloy, although it exhibits superior bondability with gold alloy. This makes it difficult to sufficiently increase the bonding strength between the portion made of titanium or titanium alloy and the portion made of ceramic.

As a result, mismatching (bumpy occlusion or the like) of the implant is apt to occur, consequently deteriorating the feeling of use of the implant.

SUMMARY

It is an object of the present invention to provide a dental implant capable of reliably preventing elution of metal when the dental implant is applied within an oral cavity and capable of reliably preventing occurrence of mismatching (bumpy occlusion or the like) when the dental implant is fixed in place, and a method for manufacturing the dental implant.

With this object in mind, one aspect of the present invention is directed to a method for manufacturing a dental implant including an abutment.

The abutment is manufactured through the steps comprising a titanium molded body production step for molding a titanium molded body composition containing powder composed of titanium or titanium alloy and a binder to obtain a titanium molded body, an assembling step for assembling the titanium molded body and a ceramic member composed of oxide-based ceramic together to obtain an assembled body, a degreasing step for degreasing the assembled body so that the binder contained in the titanium molded body is removed therefrom to transform the titanium molded body into a titanium degreased body, and a sintering step for sintering the assembled body to transform the titanium degreased body into a titanium member so that the titanium member is firmly fixed to the ceramic member.

The method of the present invention is capable of reliably preventing elution of metal when the dental implant is applied within an oral cavity and capable of reliably preventing occurrence of mismatching when the dental implant is fixed in place.

In the method of the present invention, it is preferred that the titanium molded body has a recess, and the ceramic member has a protrusion inserted into the recess.

This makes it possible to greatly increase adhesion and fixing strength between the titanium member and the ceramic member and to effectively prevent occurrence of mismatching when the dental implant is fixed in place.

In the method of the present invention, it is preferred that the recess of the titanium molded body has a size lager than that of the protrusion of the ceramic member, wherein in the assembling step, the assembled body is assembled by inserting the protrusion of the ceramic member into the recess of the titanium molded body so that a clearance is existed therebetween, and wherein in the degreasing and sintering steps, when the assembled body is degreased and sintered, the titanium molded body contracts so that the clearance is eliminated, thereby bringing the protrusion of the ceramic member into close contact with and fitting to a recess of the titanium member.

This makes it possible to greatly increase adhesion and fixing strength between the titanium member and the ceramic member and to effectively prevent occurrence of mismatching when the dental implant is fixed in place.

In the method of the present invention, it is preferred that the protrusion of the ceramic member has a portion whose cross-sectional area is increased toward a dead-end portion of the recess of the titanium molded body in a state that the protrusion of the ceramic member is inserted into the recess of the titanium molded body.

This makes it possible to greatly increase adhesion and fixing strength between the titanium member and the ceramic member and to effectively prevent occurrence of mismatching when the dental implant is fixed in place.

In the method of the present invention, it is preferred that the protrusion of the ceramic member has a portion whose cross-sectional area is continuously increased toward a dead-end portion of the recess of the titanium molded body in a state that the protrusion of the ceramic member is inserted into the recess of the titanium molded body.

This makes it possible to greatly increase adhesion and fixing strength between the titanium member and the ceramic member and to effectively prevent occurrence of mismatching when the dental implant is fixed in place.

In the method of the present invention, it is preferred that the protrusion of the ceramic member has a portion whose cross-sectional shape is non-circular.

This makes it possible to reliably prevent the titanium member and the ceramic member from making relative rotational movement and to effectively prevent occurrence of mismatching when the dental implant is fixed in place.

In the method of the present invention, it is preferred that the ceramic member is composed of zirconia as a major component thereof.

Among various kinds of oxide-based ceramics, zirconia is particularly superior in living body affinity and strength. If the ceramic member is composed of zirconia as a major component thereof, it becomes possible to remarkably improve safety of the dental implant and also to more reliably prevent occurrence of problems such as gum recession after application of the dental implant. It is also possible to greatly enhance durability of the dental implant.

Further, among various kinds of oxide-based ceramics, zirconia exhibits very low adhesion with titanium or titanium alloy. In a method using an adhesive agent or the like, therefore, adhesion and bonding strength between a member made of titanium or titanium alloy and a member made of zirconia becomes very low.

However, in the present invention, since the titanium member and the ceramic member are firmly fixed and joined together through a sintering process, it is possible to sufficiently increase adhesion and fixing strength between the titanium member and the ceramic member without using any adhesive.

In other words, effects provided by the present invention become more conspicuous if the ceramic member is composed of zirconia as a major component thereof.

In the method of the present invention, it is preferred that the ceramic member is manufactured through the steps comprising a step for molding a ceramic molded body composition containing powder composed of oxide-based ceramic and a binder to obtain a ceramic molded body, a step for degreasing the ceramic molded body by removing the binder contained in the ceramic molded body therefrom to transform the ceramic molded body into a ceramic degreased body, and a step for sintering the ceramic degreased body.

Since the oxide-based ceramic is, in general, a refractory material (a material having a high melting point), it is difficult that the oxide-based ceramic is molded by a casting or the like. However, use of the above method makes it possible to easily and accurately produce the ceramic member even if the ceramic member is of the type used in the dental implant having a minute structure.

By manufacturing the ceramic member using the above method, the ceramic member can be obtained as a porous body having a large number of fine pores. In this case, when the titanium molded body is degreased and sintered, a part of the titanium or titanium alloy constituting the titanium molded body can be diffused within the pores of the ceramic member. This makes it possible to further improve adhesion and fixing strength between the titanium member and the ceramic member.

In the method of the present invention, it is preferred that the dental implant further includes a fixture to be coupled to the abutment and anchored to a jawbone, the fixture made of titanium or titanium alloy.

This makes it possible to greatly increase fixing strength of the dental implant to a living body (a jawbone) when the dental implant is applied to the living body. It is also possible to greatly increase adhesion between the fixture and the abutment when the dental implant is applied to the living body.

In the method of the present invention, it is preferred that the ceramic member has a contact surface with which a metal having a composition different from that of a constituent material of the titanium member makes contact.

This makes it possible to reliably prevent elution of metal when the dental implant is applied within an oral cavity.

Another aspect of the present invention is directed to a dental implant including an abutment. The abutment comprises a titanium member composed of a sintered body made from titanium or titanium alloy and having a recess, and a ceramic member composed of oxide-based ceramic and having a protrusion fitted to the recess, wherein the titanium member and the ceramic member are firmly fixed and joined together through the engagement between the recess and the protrusion, and wherein this engagement state is obtained due to contraction of a non-sintered body of the titanium member through a sintering process.

The dental implant of the present invention is capable of reliably preventing elution of metal when the dental implant is applied within an oral cavity and capable of reliably preventing occurrence of mismatching when the dental implant is fixed in place.

In the dental implant of the present invention, it is preferred that the protrusion of the ceramic member has a portion whose cross-sectional area is increased toward a dead-end portion of the recess of the titanium member.

This makes it possible to greatly increase adhesion and fixing strength between the titanium member and the ceramic member and to effectively prevent occurrence of mismatching when the dental implant is fixed in place.

In the dental implant of the present invention, it is preferred that the ceramic member has a contact surface with which a metal member having a composition different from a constituent material of the titanium member makes contact.

This makes it possible to reliably prevent elution of metal when the dental implant is applied within an oral cavity.

The above and other objects, features and advantages of the present invention will become apparent from the following description of preferred embodiments given in conjunction with the accompanying drawings.

BRIEF DESCRIPTION OF THE DRAWINGS

FIGS. 3A to 3E are process views illustrating one preferred embodiment of a dental implant manufacturing method in accordance with the present invention.

DESCRIPTION OF EXEMPLARY EMBODIMENTS

Hereinafter, preferred embodiments of the present invention will be described with reference to the accompanying drawings.

Figure 1C:
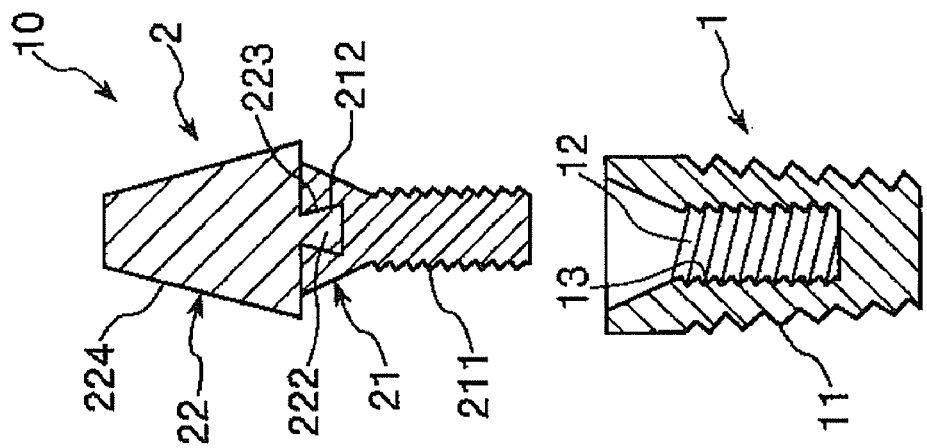
FIG. 1C is a vertical section view showing the preferred embodiment of the dental implant in which the fixture and the abutment are not threadedly coupled.
Figure 1B:
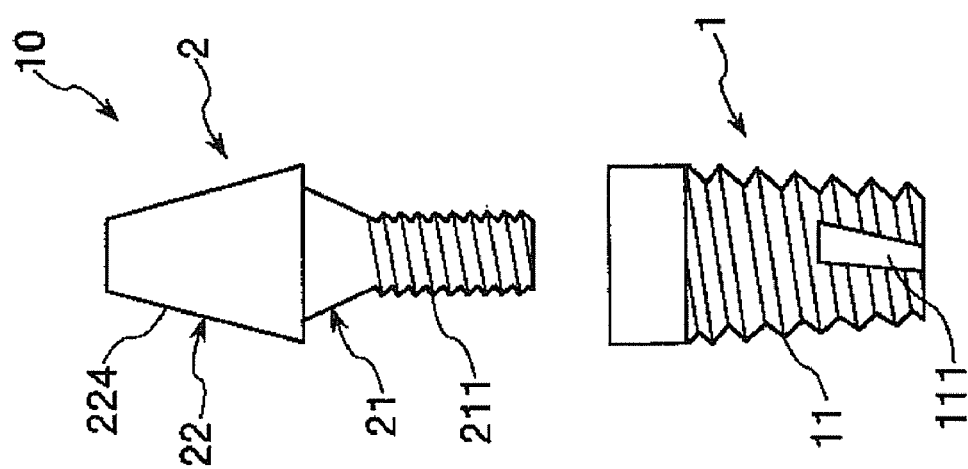
FIG. 1B is a front view showing the preferred embodiment of the dental implant in which the fixture and the abutment are not threadedly coupled.
Figure 1A:
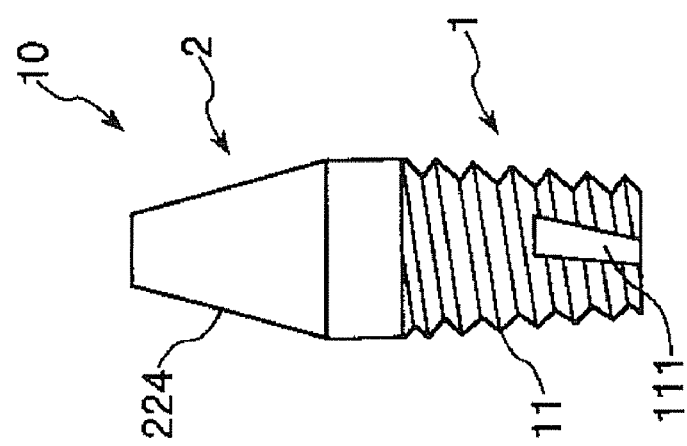
FIG. 1A is a front view showing one preferred embodiment of a dental implant in accordance with the present invention, in which a fixture and an abutment are threadedly coupled.

FIG. 1A is a front view showing one preferred embodiment of a dental implant in accordance with the present invention, in which a fixture and an abutment are threadedly coupled. FIG. 1B is a front view showing the preferred embodiment of the dental implant in which the fixture and the abutment are not threadedly coupled. FIG. 1C is a vertical section view showing the preferred embodiment of the dental implant in which the fixture and the abutment are not threadedly coupled.

Figure 2A:
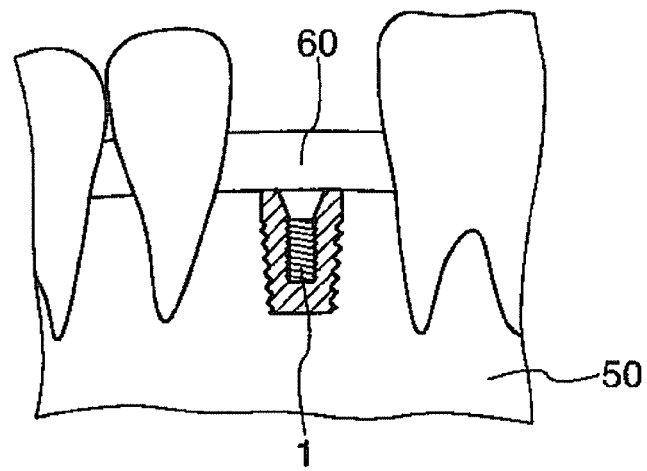
FIGS. 2A to 2C are views for explaining an operation method using the dental implant.
Figure 2B:
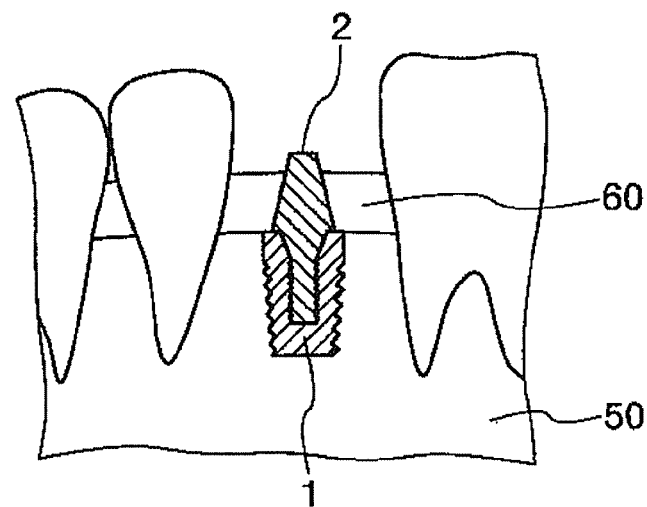
Figure 2C:
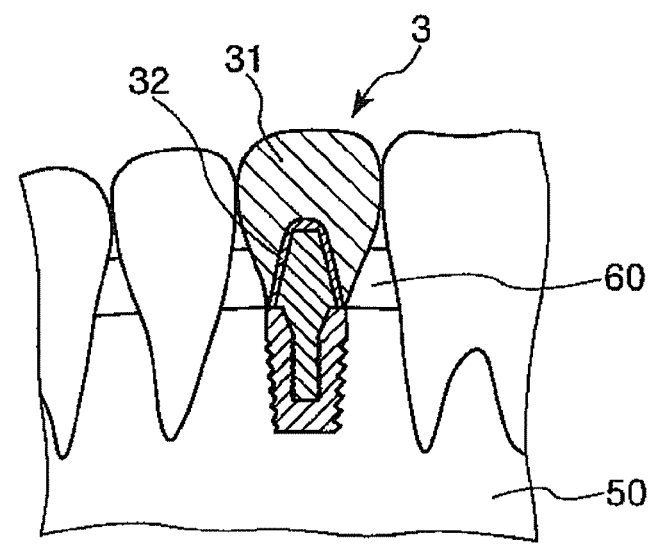

FIGS. 2A to 2C are views for explaining an operation method using the dental implant. FIGS. 3A to 3E are process views illustrating one preferred embodiment of a dental implant manufacturing method in accordance with the present invention.

Figure 4B:
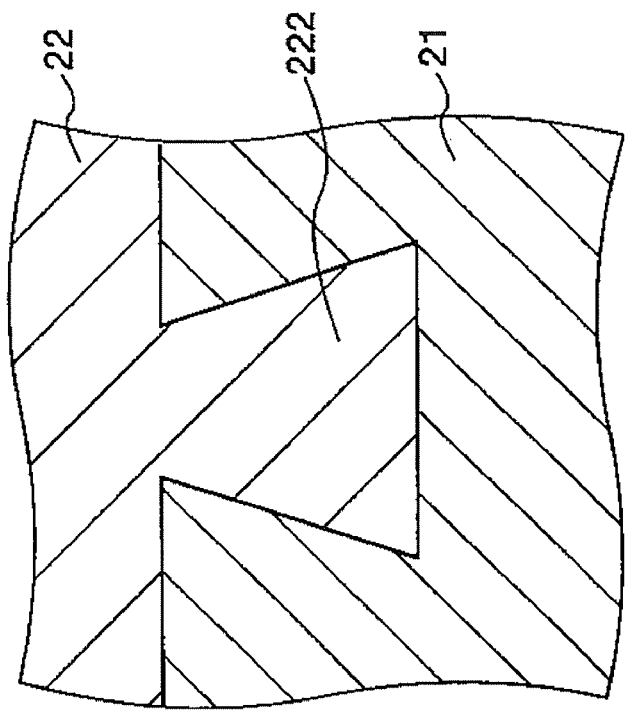
FIG. 4B is a vertical section view showing a boundary portion between a titanium member and a ceramic member after a sintering step has been performed.
Figure 4A:
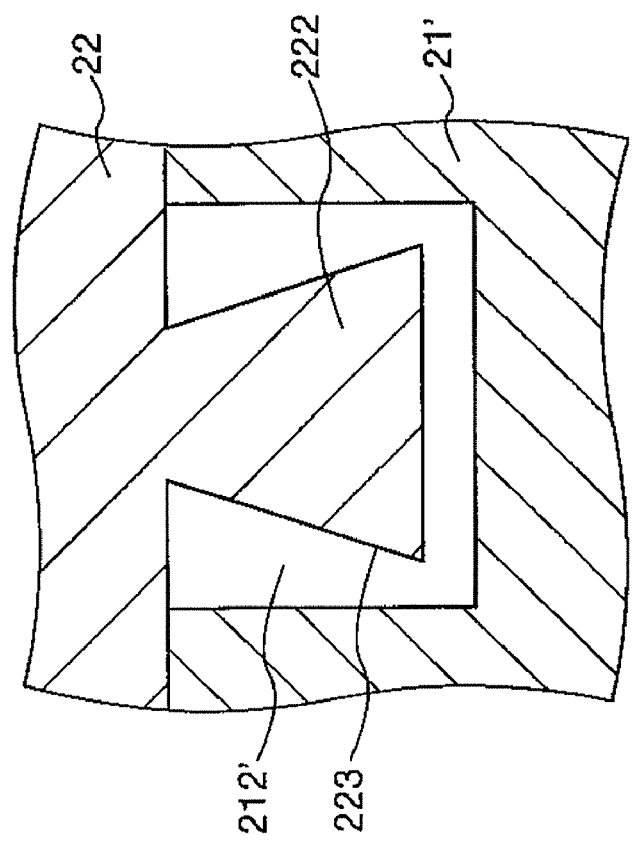
FIG. 4A is a vertical section view showing a boundary portion between a titanium molded body and a ceramic member which are kept in an assembled state.

FIG. 4A is a vertical section view showing a boundary portion between a titanium molded body and a ceramic member which are kept in an assembled state. FIG. 4B is a vertical section view showing a boundary portion between a titanium member and a ceramic member after a sintering step has been performed.

The drawings referred to in this specification show parts of components in an exaggerated state and does not accurately reflect the actual dimension thereof.

Dental Implant

First, description will be made on a dental implant in accordance with the present invention.

A dental implant 10 includes a fixture 1 anchored to a jawbone and an abutment 2 threadedly coupled to the fixture 1.

(1) Fixture

The fixture 1 is a member that will be anchored to the jawbone in an operation using the dental implant 10. The fixture 1 is formed into a bottom-closed tubular shape. A male thread portion 11 is provided on an outer circumferential surface of the fixture 1. This makes it possible to threadedly anchor the fixture 1 to the jawbone in which a thread is formed by cutting or other methods.

A cutout portion 111 having a specified length is formed in a part of the male thread portion 11 to extend in an axial direction of the fixture 1. No spiral groove is formed in the cutout portion 111. This makes it possible to threadedly anchor the fixture 1 to the jawbone in an easy and reliable manner during a course of conducting an operation.

After the operation comes to an end, osteogenesis is progressed by osteoblastic cells in a region of a living body corresponding to the cutout portion 111. Therefore, it is possible to effectively prevent the thread coupling from being loosened.

The fixture 1 has a tubular portion 12 into which the abutment 2 is inserted as mentioned below. Formed on an inner circumferential surface of the fixture 1 is a female thread portion 13 that can make thread coupling with a male thread portion 211 of the abutment 2 (a titanium member 21).

The fixture 1 may be made of any material. From the standpoint of living body compatibility, strength and so forth, it is preferred that the fixture 1 is made of titanium or titanium alloy.

(2) Abutment

The abutment 2 is a member that will be fixed to the fixture 1 in the operation using the dental implant 10. Further, the abutment 2 is capped by a crown restoration 3 which is used for a purpose of improving aesthetic appearance and assuring enhanced occlusion.

The abutment 2 includes a titanium member 21 made of titanium or titanium alloy and a ceramic member 22 made of oxide-based ceramic.

(2.1) Titanium Member

The titanium member 21 is one of constituent members of the abutment 2 that will be threadedly coupled to the female thread portion 13 of the fixture 1 as mentioned above. The titanium member 21 has a male thread portion 211 threadedly coupled to the female thread portion 13 of the fixture 1.

The titanium member 21 is made of titanium or titanium alloy. It is preferred that the titanium member 21 is made of a material having the same composition as that of a constituent material of the fixture 1. This makes it possible to greatly improve adhesion between the fixture 1 and the abutment 2.

Furthermore, this makes it possible to reliably prevent occurrence of problems such as elution of metal within an oral cavity due to a galvanic cell formed by an electric potential difference between the constituent material of the fixture 1 and the constituent material of the abutment 2.

Further, the titanium member 21 has a recess 212 to which a protrusion 222 formed in the ceramic member 22 is to be fitted as mentioned below. The recess 212 is of a shape complementary to the protrusion 222 of the ceramic member 22.

The titanium member 21 is firmly fixed and joined to the ceramic member 22 through a joint (engagement) between the protrusion 222 and the recess 212. For this reason, the titanium member 21 and the ceramic member 22 exhibit extremely superior adhesion between them.

(2.2) Ceramic Member

The ceramic member 22 is a member capped by a crown restoration 3 as mentioned below. The ceramic member 22 has the protrusion 222 fitted to the titanium member 21 as mentioned above.

The protrusion 222 is of a shape complementary to the recess 212 of the titanium member 21, thereby keeping adhesion between the titanium member 21 and the ceramic member 22 extremely high.

The protrusion 222 has a cross-sectional area increasing portion 223 whose cross-sectional area is increased from a base end toward a distal end of the protrusion 222, that is, toward a dead-end portion of the recess 212 of the titanium member 21.

Provision of the cross-sectional area increasing portion 223 makes it possible to greatly enhance adhesion and fixing strength (joint strength) between the titanium member 21 and the ceramic member 22. It is also possible to more effectively prevent any mismatching (bumpy occlusion or the like) when the dental implant 10 is fixed in place.

Although the cross-sectional area increasing portion 223 may be formed in such a manner that the cross-sectional area of the protrusion 222 is increased either continuously or noncontinuously toward the distal end thereof, it is preferred that the cross-sectional area is increased continuously as shown in the drawings.

This makes it possible to greatly enhance adhesion and fixing strength between the titanium member 21 and the ceramic member 22. It is also possible to more effectively prevent any mismatching when the dental implant 10 is fixed in place.

An angle θ between a surface (a circumferential surface) of the cross-sectional area increasing portion 223 and a heightwise axis of the protrusion 222 is not particularly limited to a specific value, but is preferably in the range of 0.3 to 5°, and more preferably in the range of 1 to 4°.

By setting the angle θ within the above ranges, the titanium member 21 is prevented from becoming extremely thin in a region around the recess 212 of the titanium member 21. As a result, an effect provided by the cross-sectional area increasing portion 223 grows conspicuous.

In other words, it is possible to greatly enhance adhesion and fixing strength between the titanium member 21 and the ceramic member 22 while keeping strength of the titanium member 21 sufficiently high. As a consequence, it is possible to keep durability of the dental implant 10 sufficiently high and also to more effectively prevent any mismatching when the dental implant 10 is fixed in place.

In contrast, if the angle θ is smaller than the lower limit value noted above, there is a possibility that the effect provided by the cross-sectional area increasing portion 223 may not be sufficiently attained.

On the other hand, if the angle θ exceeds the upper limit value noted above, there is a possibility that the titanium member 21 may have a region with no sufficiently great thickness (a thin region) around the recess 212 to which the protrusion 222 of the ceramic member 22 is fitted. This may reduce strength and durability of the dental implant 10.

In the illustrated configuration, the cross-sectional area increasing portion 223 is formed over a full heightwise length of the protrusion 222. This makes it possible to greatly enhance adhesion and fixing strength between the titanium member 21 and the ceramic member 22. It is also possible to more effectively prevent any mismatching when the dental implant 10 is fixed in place.

Furthermore, it is preferred that the protrusion 222 has a portion whose cross-sectional shape is non-circular. This makes it possible to more reliably prevent the titanium member 21 and the ceramic member 22 from making relative rotational movement. It is also possible to more effectively prevent any mismatching when the dental implant 10 is fixed in place.

In this regard, examples of the non-circular shape include a generally polygonal shape such as a triangular shape, a rectangular shape, a hexagonal shape or the like, a partially cutaway circular shape, an elliptical shape and so forth.

A height of the protrusion 222 is not particularly limited to a specific value, but is preferably in the range of 2 to 5 mm, and more preferably in the range of 3 to 4 mm. This makes it possible to greatly increase strength and durability of the abutment 2.

Further, the ceramic member 22 has a metal bonding surface (a contact surface) 224 that makes contact with a metal portion 32 of the crown restoration 3 when the dental implant 10 is capped by the crown restoration 3 as mentioned below.

As set forth above, the ceramic member 22 is made of oxide-based ceramic. Among various kinds of materials (especially, various kinds of ceramic materials), the oxide-based ceramic is particularly superior in living body compatibility and extremely low in living body hazard. Furthermore, the oxide-based ceramic seldom gathers contaminants and exhibits increased hardness and strength.

Examples of the oxide-based ceramic of which the ceramic member 22 is made include zirconia (zirconium oxide), silicon oxide (silica), aluminum oxide (alumina), calcium oxide, sodium oxide, potassium oxide, boron oxide, zinc oxide, magnesium oxide (magnesia), lithium oxide, tin oxide, indium oxide and titanium oxide, one or more of which may be used independently or in combination.

Among them, it is preferred that the ceramic member 22 is composed of zirconia as a major component thereof. Among various kinds of oxide-based ceramics, zirconia is particularly superior in living body affinity and strength.

If the ceramic member 22 is composed of zirconia as a major component thereof, it becomes possible to remarkably improve safety of the dental implant 10 and also to more reliably prevent occurrence of problems such as gum recession and the like after application of the dental implant 10. It is also possible to greatly enhance durability of the dental implant 10.

Further, among various kinds of oxide-based ceramics, zirconia exhibits very low adhesion with titanium or titanium alloy. In a method using an adhesive agent or the like, therefore, adhesion and bonding strength between a member made of titanium or titanium alloy and a member composed of zirconia becomes very low.

However, in the present invention, since the titanium member and the ceramic member are firmly fixed and joined together through a sintering process, it is possible to sufficiently increase adhesion and fixing strength between the titanium member and the ceramic member without using any adhesive.

In other words, effects provided by the present invention become more conspicuous if the ceramic member is composed of zirconia_as a major component thereof.

In this regard, it is to be noted that the term "as a major component thereof" used herein means that a particular component of a material constituting a subject member or composition has the greatest content.

A content of the component is not particularly limited to a specific value, but is preferably 50 wt % or more, more preferably 55 wt % or more, and even more preferably 60 wt % or more of the material constituting the subject member or composition.

Operation Method Using Dental Implant

Next, an operation method using the dental implant 10 will be described with reference to FIGS. 2A to 2C.

Embedding Fixture

After putting a patient under anesthesia, the fixture 1 is threadedly anchored to a jawbone 50 in which a thread is cut in advance (see FIG. 2A). Then, the fixture 1 is covered with a gum 60 if necessary.

Threadedly Coupling Abutment

If osteogenesis is adequately progressed by osteoblastic cells and osteointegration between the fixture 1 and the jawbone 50 is progressed sufficiently after the lapse of a specified time period (usually about 3 to 6 months) from the fixture embedding time, the abutment 2 is threadedly coupled to the fixture 1 anchored to the jawbone 50 (see FIG. 2B).

In the case where the fixture 1 is covered with the gum 60, the fixture 1 is exposed as appropriate by incising the gum 60 prior to threadedly coupling the abutment 2.

Capping Crown Restoration

Next, the crown restoration 3 molded by modeling is fixed to the ceramic member 22 of the abutment 2 (see FIG. 2C). The crown restoration 3 includes a ceramic portion 31 made of ceramic and visually recognized from the outside after performing this operation, and a metal portion 32 made of a metallic material and provided on an inner surface of the ceramic portion 31.

The crown restoration 3 of this configuration exhibits good appearance at the end of the operation and is capable of improving occlusion and reliably preventing occurrence of a crack or other defects in the crown restoration 3.

Examples of the ceramic of which the ceramic portion 31 is made include silicon oxide (silica), aluminum oxide (alumina), calcium oxide, sodium oxide, potassium oxide, boron oxide, zinc oxide, magnesium oxide (magnesia), lithium oxide, tin oxide, indium oxide and titanium oxide.

On the other hand, the metallic material of which the metal portion 32 is made has a composition different from that of the constituent material of the titanium member 21. In general, gold or gold alloy is used as the metallic material.

If the metal portion 32 is made of gold or gold alloy, effects of improving occlusion and preventing occurrence of a crack or other defects in the crown restoration 3 become more conspicuous.

The crown restoration 3 is capped on the abutment 2 so that the metal portion 32 makes contact with the metal bonding surface 224 of the ceramic member 22. Although the metal portion 32 comes into contact with the ceramic member 22 (the metal bonding surface 224) at this time, it does not make contact with the titanium member 21 and the fixture 1. If desired, it may be possible to use dental cement in bonding the abutment 2 and the crown restoration 3 together.

In the case where the gum 60 is incised during the abutment coupling process, it is general that this process of capping the crown restoration 3 is not performed until disappearance of tumescence of the gum 60 is confirmed over a time period of about 1 to 6 weeks after the abutment coupling process.

Dental Implant Manufacturing Method

Next, description will be made on a method for manufacturing the dental implant 10 set forth above.

Titanium Molded Body Production Step

First, a titanium molded body 21' is obtained by molding a titanium molded body composition that contains powder composed of titanium or titanium alloy and a binder (see FIG. 3A).

Hereinafter, the titanium molded body composition will be described in detail.

Powder

An average particle size of powder (metal powder) of which the titanium molded body composition is composed is not particularly limited to a specific value, but is preferably in the range of 0.3 to 100 μm, and more preferably in the range of 0.5 to 50 μm.

If the average particle size of the powder falls within the range noted above, it becomes possible to produce the titanium molded body 21' and the titanium member (sintered body) 21 with increased moldability (ease of molding), wherein the titanium member 21 is produced by degreasing and sintering the titanium molded body 21'.

It is also possible to increase density of the titanium member 21 thus obtained and to improve properties of the sintered body such as mechanical strength, dimensional accuracy and the like.

In contrast, if the average particle size of the powder is smaller than the lower limit value noted above, moldability of the titanium molded body 21' exhibits a decrease. If the average particle size of the powder exceeds the upper limit value noted above, it is difficult to sufficiently increase density of the titanium member 21, which may possibly lead to deterioration in properties of the titanium member 21.

The term "average particle size" used herein refers to a particle size of powder distributed at a point of 50% in terms of an accumulated volume in a particle size distribution of subject powder.

Although the power may be produced by any method, it is possible to use powder obtained by, e.g., various kinds of atomizing methods including a liquid atomizing method such as a water-atomizing method or the like (e.g., a fast-rotating water stream atomizing method and a rotating-liquid atomizing method) and a gas atomizing method, a pulverizing method, a hydrogenation method and a hydrogenation-dehydrogenation method.

A content percentage of the powder contained in the titanium molded body composition (the titanium molded body 21') is not particularly limited to a specific value, but is preferably in the range of 60 to 97 wt %, and more preferably in the range of 65 to 95 wt %.

If the content percentage of the powder is smaller than the lower limit value noted above, it is likely that the titanium member 21 obtained exhibits reduction in its mechanical strength and dimensional stability.

In contrast, if the content percentage of the powder exceeds the upper limit value noted above, the content percentage of the below-mentioned binder is reduced correspondingly. Thus, the titanium molded body composition exhibits reduced flowability during the molding process, which may possibly reduce operability.

Furthermore, it may possibly become difficult to sufficiently increase fixing strength of the titanium member 21 relative to the ceramic member 22 in the abutment 2 finally obtained.

Binder

The binder is a component that heavily affects moldability (ease of molding) of the titanium molded body composition and stability in shape (shape-keeping ability) of the titanium molded body 21' and a titanium degreased body 21" which is obtained by degreasing the titanium molded body 21' as mentioned below.

If the titanium molded body composition contains such a component, it becomes possible to easily and reliably produce the titanium member 21 as a sintered body with increased dimensional accuracy.

Examples of the binder include: various kinds of resin such as polyolefin (e.g., polyethylene, polypropylene and ethylene-vinyl acetate copolymer), acrylic resin (e.g., polymethylmethacrylate and polybuthylmethacrylate), styrene-based resin (e.g., polystyrene), polyvinyl chloride, polyvinylidene chloride, polyamide, polyester (e.g., polyethylene terephthalate and polybutylene terephthalate), polyether, polyvinyl alcohol, polypropylene carbonate or copolymer thereof; various kinds of wax; paraffin; higher fatty acid (e.g., stearic acid); higher alcohol; higher fatty acid ester; higher fatty acid amide; and the like. One or more of these substances may be used independently or in combination.

A content percentage of the binder contained in the titanium molded body composition (the titanium molded body 21') is preferably in the range of 3 to 40 wt %, and more preferably in the range of 5 to 35 wt %.

If the content percentage of the binder is smaller than the lower limit value noted above, it is likely that the titanium molded body composition exhibits reduced flowability during the molding process, which may possibly reduce operability.

Furthermore, it may possibly become difficult to sufficiently increase fixing strength of the titanium member 21 relative to the ceramic member 22 in the abutment 2 finally obtained.

In contrast, if the content percentage of the binder exceeds the upper limit value noted above, there is a possibility that the titanium member 21 obtained exhibits reduction in its mechanical strength and dimensional stability.

Other Components

Other components may be contained in the titanium molded body composition in addition to the above-mentioned components. Examples of such components include a dispersant (lubricant), a plasticizer and an antioxidant, one or more of which may be used independently or in combination. This allows the titanium molded body composition to exhibit functions inherent in the respective components.

If the titanium molded body composition contains the dispersant among these components, the dispersant adheres to the powder. This makes it possible to improve dispersibility of the powder in the titanium molded body composition.

Consequently, the titanium degreased body 21" and the titanium sintered body (titanium member 21) to be obtained in subsequent steps exhibit particularly high uniform composition (constitution) and property in each and every portion thereof.

If the titanium molded body composition contains the dispersant, it is also possible to greatly improve flowability of the titanium molded body composition when molding the titanium molded body 21' and to increase mold-filling ability thereof. This makes it possible to more reliably obtain a titanium molded body 21' having uniform density.

Examples of the dispersant include: an anionic organic dispersant such as higher fatty acid (e.g., stearic acid, distearic acid, tristearic acid, linolenic acid, octanoic acid, oleic acid, palmitic acid and naphthenic acid), polyacrylic acid, polymethacrylic acid, polymaleic acid, acrylic acid-maleic acid copolymer or polystyrene sulfonic acid; a cationic organic dispersant such as quaternary ammonium acid; a non-ionic organic dispersant such as polyvinyl alcohol, carboxymethyl cellulose or polyethylene glycol; an inorganic dispersant such as tricalcium phosphate; and the like.

Among the above-noted substances, it is preferred that the dispersant is composed of the higher fatty acid as a major component thereof. This is because the higher fatty acid exhibits particularly high powder dispersibility.

Furthermore, a carbon number of the higher fatty acid is preferably in the range of 16 to 30, and more preferably in the range of 16 to 24. If the carbon number of the higher fatty acid falls within the above range, the titanium molded body composition exhibits improved shape-keeping ability with no reduction in moldability.

Additionally, if the carbon number of the higher fatty acid falls within the above range, the higher fatty acid can be easily decomposed at a relatively low temperature.

If the titanium molded body composition contains the plasticizer, it becomes possible to greatly improve plasticity and moldability of the titanium molded body composition. As a result, it is possible to increase mold-filling ability and to more reliably obtain a titanium molded body 21' having uniform density.

Examples of the plasticizer include phthalic acid ester (e.g., DOP, DEP and DBP), adipic acid ester, trimellitic acid ester, sebacic acid ester and the like.

The antioxidant has a function of preventing oxidation of resin of which the binder is composed. Examples of the antioxidant include a hindered phenol-based antioxidant, hydrazine-based antioxidant, and the like.

The titanium molded body composition containing the respective components set forth above can be prepared by, e.g., mixing various kinds of powder corresponding to the components.

If desired, kneading may be performed after the various kinds of powder are mixed. This makes it possible to increase flowability of the titanium molded body composition and to improve homogeneity thereof.

Therefore, it is possible to obtain a titanium molded body 21' having higher density and sufficient homogeneity. As a result, dimensional accuracy of the titanium degreased body 21" and the titanium sintered body (the titanium member 21) can be improved.

The kneading of the mixture can be performed by various kinds of kneading machines such as a pressure type or dual-arm kneader type kneading machine, a roller type kneading machine, a Banbury type kneading machine, and a single-axis or dual-axis extruding machine.

Kneading conditions depend on the particle size of the powder used, the composition of the binder, the blending quantity of the powder and the binder and so forth. As an example, the kneading condition can be set to a condition in that a kneading temperature is in the range of 50 to 200° C. and a kneading time is in the range of 15 to 210 minutes.

If necessary, a kneaded product (compound) obtained is pulverized into pellets (small masses). A diameter of pellets may be set to the range of about 1 to 10 mm. A pulverizing device such as a pelletizer or the like can be used in pelletizing the kneaded product.

The titanium molded body 21' (a non-sintered body of the titanium member 21) is obtained by molding the titanium molded body composition through use of a required molding method. Although the molding method of the titanium molded body 21' is not particularly limited to a specific method, an injection molding method is generally used because the titanium molded body 21' to be molded has a small size and a complex shape.

At the end of the injection molding process, the molded body thus obtained may be subjected to machining, electric discharging, laser processing, etching and so forth in order to remove burrs or to form a minute structure such as a groove or the like.

The molded body obtained by use of the titanium molded body composition contains the binder in a relatively high content percentage. Therefore, the molded body is easier to process than the titanium degreased body 21" and the titanium sintered body (the titanium member 21) which will be set forth below. This means that the molded body can be easily subjected to the above processing.

Assembling Step

Next, the titanium molded body 21' obtained in the above manner and the ceramic member 22 composed of oxide-based ceramic are assembled together to obtain an assembled body (see FIG. 3B).

In the present step, the titanium molded body 21' and the ceramic member 22 are assembled together by inserting the protrusion 222 of the ceramic member 22 into the recess 212' of the titanium molded body 21' (corresponding to the recess 212 of the titanium member 21) as illustrated in FIG. 4A.

A clearance with a sufficiently great width exists between the recess (a non-contracted recess) 212' of the titanium molded body 21' and the protrusion 222 of the ceramic member 22. This reliably prevents the titanium molded body 21' from undergoing inadvertent deformation, e.g., when the protrusion 222 is inserted into the recess 212'.

A method of manufacturing the ceramic member 22 to be used in this step is not particularly limited to a specific method. It is preferred that the ceramic member 22 is manufactured through the steps including a molding step (a ceramic molded body production step) for molding a ceramic molded body composition containing powder (ceramic powder) composed of the oxide-based ceramic and a binder to obtain a ceramic molded body, a degreasing step (a ceramic molded body degreasing step) for degreasing the ceramic molded body by removing the binder contained in the ceramic molded body therefrom to transform it into a ceramic degreased body, and a sintering step (a ceramic degreased body sintering step) for sintering the ceramic degreased body.

Since the oxide-based ceramic is, in general, a refractory material (a material having a high melting point), it is difficult that the oxide-based ceramic is molded by a casting or the like. However, use of the above method makes it possible to easily and accurately produce the ceramic member 22 even if the ceramic member 22 is of the type used in the dental implant 10 having a minute structure.

By manufacturing the ceramic member 22 using the above method, the ceramic member 22 can be obtained as a porous body having a large number of fine pores. In this case, when the titanium molded body 21' is degreased and sintered, a part of the titanium or titanium alloy constituting the titanium molded body 21' can be diffused within the pores of the ceramic member 22. This makes it possible to further improve adhesion and fixing strength between the titanium member 21 and the ceramic member 22.

In the case where the ceramic member 22 is manufactured by the above method, it is possible to produce the ceramic molded body in the same manner as available in molding the titanium molded body described earlier except that powder composed of the oxide-based ceramic is used instead of the powder composed of the titanium or titanium alloy.

Furthermore, a degreasing process and a subsequent sintering process for the ceramic molded body can be performed by the same method as a degreasing process and a subsequent sintering process for the titanium molded body 21' (which will be described below in detail) except that their processing temperatures are different from each other.

In this regard, the processing temperature of the degreasing process for the ceramic molded body is preferably in the range of 100 to 780° C., and more preferably in the range of 150 to 720° C. Further, the processing temperature of the sintering process for the ceramic degreased body is preferably in the range of 1250 to 1900° C., and more preferably in the range of 1300 to 1800° C.

Moreover, in the case where the ceramic member 22 is manufactured by the above method, the ceramic molded body, the ceramic degreased body or the sintered body may be subjected to machining, electric discharging, laser processing, etching and so forth.

Degreasing Step (Titanium Molded Body Degreasing Step)

Next, the assembled body formed of the titanium molded body 21' and the ceramic member 22 is subjected to a degreasing process. By doing so, the binder contained in the titanium molded body 21' is removed therefrom to transform the titanium molded body 21' into a titanium degreased body 21" (see FIG. 3C).

A method for the degreasing process is not particularly limited to a specific method. Examples of the method for the degreasing process include a heat treatment either in a non-oxidant atmosphere, e.g., in a vacuum or depressurized state (of, e.g., $1 \times 10^{-1}$ to $1 \times 10^{-6}$ Torr or 13.3 to $1.33 \times 10^{-4}$ Pa) or under the presence of a gas such as a nitrogen gas, an argon gas and the like.

A processing temperature in the degreasing (heat treatment) step is not particularly limited to a specific value, but is preferably in the range of 100 to 750° C., and more preferably in the range of 150 to 700° C.

Further, a processing (heat treatment) time in the degreasing (heat treatment) step is not particularly limited to a specific value, but is preferably in the range of 0.5 to 20 hours, and more preferably in the range of 1 to 10 hours.

In this regard, it is to be noted that the degreasing process using the heat treatment may be performed through a plurality of steps for different purposes (e.g., for the purpose of shortening the degreasing time).

In this case, it may be possible to use, e.g., a method by which a former half of the degreasing process is performed at a low temperature and a latter half of the degreasing process is performed at a high temperature, a method by which a low-temperature degreasing process and a high-temperature degreasing process are performed alternately, or the like.

At the end of the degreasing process, the thus obtained titanium degreased body 21" may be subjected to machining, electric discharging, laser processing, etching and so forth in order to remove burrs or to form a minute structure such as a groove or the like. The titanium degreased body 21" is easier to process than the titanium member 21 (the sintered body).

In this regard, it is to be noted that the binder contained in the titanium molded body 21' may not be completely removed therefrom. Namely, a part of the binder may remain in the titanium degreased body 21" at the point that the degreasing process has been completed.

Sintering Step (Titanium Degreased Body Sintering Step)

Next, the assembled body thus degreased is subjected to a sintering process, whereby the titanium degreased body 21" (a non-sintered body of the titanium member 21) is transformed into the titanium member (sintered body) 21. Thus, the titanium member 21 is firmly fixed and joined to the ceramic member 22 (see FIG. 3D). This provides the abutment 2 in which the titanium member 21 and the ceramic member 22 are fixedly joined together.

As described above, one of the features of the present invention resides in that the titanium member is firmly fixed and joined to the ceramic member by subjecting the assembled body consisting of the ceramic member and the titanium molded body to the degreasing process and the sintering process.

Alternatively, it would be conceivable that a ceramic member and a titanium member are independently produced and bonded together by use of, e.g., dental cement. However, in general, titanium or titanium alloy exhibits inferior bondability (adhesiveness) with respect to ceramic. Therefore, if the ceramic member and the titanium member are merely bonded together by the use of the dental cement, it is impossible to attain sufficiently high bonding strength therebetween. It is also likely that a dental implant is destroyed after its application to a living body.

As a further alternative, it would be conceivable that an adhesive agent stronger than the generally available dental cement is used in bonding a ceramic member and a titanium member together. In this case, however, there exists a hazard that a component contained in the adhesive agent may adversely affect the living body to which a dental implant is applied.

The titanium member 21 is formed due to contraction of the titanium molded body 21' through the degreasing process and the sintering process. As a result of this contraction, as shown in FIG. 4B, the recess (a contracted recess) 212 of the titanium member 21 becomes a shape corresponding to an external shape (a surface shape) of the protrusion 222 of the ceramic member 22 so that the protrusion 222 is in close contact with and fitted to the recess 212.

In other words, a clearance that has existed between the titanium molded body 21' (the recess 212') and the ceramic member 22 (the protrusion 222) in the assembling process thereof is eliminated by degreasing and sintering the titanium molded body 21', thereby bringing the titanium member 21 into close contact with the ceramic member 22. Consequently, the titanium member 21 is firmly fixed to the ceramic member 22 so that the titanium member 21 and the ceramic member 22 can be kept in an inseparable state.

Particularly, the ceramic member 22 used in the present embodiment has the cross-sectional area increasing portion 223 set forth above. Therefore, even if a relatively great tensile force is imparted in a direction parallel to a direction of a height of the protrusion 222 (a direction of depth of the recess 212), it is possible to keep the titanium member 21 and the ceramic member 22 in a fixedly coupled state.

A method for the sintering process is not particularly limited to a specific method. Examples of the method for the sintering process include a heat treatment either in a non-oxidant atmosphere, e.g., in a vacuum or depressurized state (of, e.g., $1\times10^{-2}$ to $1\times10^{-6}$ Torr or 133 to $1.33\times10^{-4}$ Pa) or under the presence of a gas such as a nitrogen gas, an argon gas and the like.

The atmosphere in which the sintering step is performed may be changed in the midst of the step. For example, the sintering atmosphere may be a depressurized atmosphere at the outset and may be changed to an inert atmosphere in the middle of the sintering step.

Furthermore, the sintering step may be divided into two or more steps. This makes it possible to improve sintering efficiency and to shorten a sintering time.

It is preferred that the sintering step is performed just after the degreasing step. This allows the degreasing step to serve as a pre-sintering step in which the degreased body (the titanium degreased body 21") is pre-heated. This ensures that the degreased body is sintered in a reliable manner.

A processing temperature in the sintering (heat treatment) step is not particularly limited to a specific value, but is preferably in the range of 1000 to 1400° C., and more preferably in the range of 1050 to 1260° C.

In general, titanium or titanium alloy has a melting point sufficiently lower than that of oxide-based ceramic of which the ceramic member 22 is composed. For this reason, the assembled body can be subjected to the sintering process at a relatively low temperature.

At this time, any undesirable deformation of the ceramic member 22 can be prevented reliably. As a result, it is possible to obtain an abutment 2 having high dimensional accuracy.

A processing (heat treatment) time in the sintering (heat treatment) step is preferably in the range of 0.5 to 20 hours, and more preferably in the range of 1 to 15 hours.

In this regard, it is to be noted that the degreasing process using the heat treatment may be performed through a plurality of steps for different purposes (e.g., for the purpose of shortening the sintering time).

In this case, it may be possible to use, e.g., a method by which a former half of the sintering process is performed at a low temperature and a latter half of the sintering process is performed at a high temperature or a method by which a low-temperature sintering process and a high-temperature sintering process are performed alternately.

At the end of the sintering process, the sintered body thus obtained may be subjected to machining, electric discharging, laser processing, etching and so forth in order to remove burrs or to form a minute structure such as a groove or the like. As compared to the titanium molded body 21' and the titanium degreased body 21", the sintered body is closer in shape and size to the titanium member 21 to be produced.

This means that dimensional accuracy of the titanium member 21 finally obtained by processing the sintered body is greater than that of the titanium member 21 produced by subjecting the titanium molded body 21' or the titanium degreased body 21" to machining, electric discharging, laser processing, etching and so forth.

Production of Fixture

The fixture 1 is produced independently of the production of the abutment 2. A method of producing the fixture 1 is not particularly limited to a specific method.

It is preferred that the fixture 1 is produced by a method which includes a molding step (a molded fixture body production step) for molding a molded body composition containing powder composed of a constituent material of the fixture 1 and a binder to obtain a molded fixture body, a degreasing step (a molded fixture body degreasing step) for degreasing the molded fixture body by removing the binder contained in the molded fixture body therefrom to transform it into a degreased fixture body, and a sintering step (a degreased fixture body sintering step) for sintering the degreased fixture body.

Use of this method makes it possible to easily and accurately produce the fixture 1 even if the fixture 1 is of the type used in the dental implant 10 having a minute structure. In the case where the fixture 1 is produced by the above method, it is possible to produce the molded fixture body in the same manner as available in molding the titanium molded body described earlier.

Furthermore, the degreasing process and the subsequent sintering process for the molded fixture body can be performed by the same method and in the same conditions as described above with regard to the degreasing step (titanium molded body degreasing step) and the sintering step (titanium degreased body sintering step).

The dental implant 10 is obtained by producing the fixture 1 and the abutment 2 in the above-described manner (see FIG. 3E).

While a preferred embodiment of the present invention has been described above, the present invention is not limited thereto. For example, an arbitrary step may be optionally added to the method of manufacturing the dental implant (particularly, the abutment).

Furthermore, although the dental implant includes the fixture and the abutment in the embodiment described above, it may have other structures as long as the titanium member and the ceramic member are fixed together in the above-mentioned manner. As an example, the dental implant of the present invention may be comprised of only the titanium member and the ceramic member.

Moreover, although the ceramic member to be used for assembling the assembled body is produced through the degreasing process and the sintering process in the embodiment described above, the ceramic member may be produced by any method.

Further, the ceramic member may be a ceramic molded body or a ceramic degreased body which is not sintered sufficiently, that is, the ceramic member may be a ceramic preliminary sintered body. Even in this case, when the assembled body is subjected to the degreasing process and the sintering process, the ceramic preliminary sintered body can be transformed into the ceramic sintered body.

EXAMPLES

Next, description will be made on specific examples of the present invention.

1. Manufacture of Dental Implant

Example 1

1-1. Production of Fixture

Prepared first was titanium powder with an average particle size of 20 μm, which was produced by a gas atomizing method.

A binder composed of 2.7 wt % of polystyrene (PS), 2.7 wt % of ethylene-vinyl acetate copolymer (EVA) and 2.3 wt % of paraffin wax and 1.3 wt % of dibutylphthalate (plasticizer) were mixed with 91 wt % of the titanium powder to obtain a mixture.

The mixture was kneaded by a pressure type kneader (kneading machine) under the conditions of a kneading temperature of 100° C. and a kneading time of 60 min to obtain a kneaded product. This kneading was carried out in a nitrogen atmosphere.

Next, the kneaded product was pulverized into pellets with an average particle size of 5 mm. The pellets were put into an injection molding machine, and injected into a mold provided in the machine and having an internal shape corresponding to an external shape of the fixture to be produced under the molding conditions of a material temperature of 130° C. and an injection pressure of 10.8 MPa (110 kgf/cm$^2$) to obtain a molded fixture body within the mold. Thereafter, the molded fixture body was ejected from the mold. This process was repeatedly performed to obtain a specified number of the molded fixture bodies.

The molded fixture bodies thus obtained were degreased under the conditions of a degreasing temperature of 450° C., a degreasing time of one hour and a degreasing atmosphere of nitrogen gas (set to the atmospheric pressure), so that the binder contained in the molded fixture bodies was removed therefrom to transform them into degreased fixture bodies.

Then, under the conditions of a sintering temperature of 1200° C., a sintering time of three hours and a vacuum sintering atmosphere, the degreased fixture bodies were sintered to obtain sintered bodies.

Subsequently, the sintered bodies thus obtained were machined so that cutout portions (see FIG. 1A) were formed to produce fixtures as desired.

1-2. Production of Abutment

Titanium Molded Body Production Step

Prepared first was titanium powder with an average particle size of 20 μm, which was produced by a gas atomizing method.

A binder composed of 2.7 wt % of polystyrene (PS), 2.7 wt % of ethylene-vinyl acetate copolymer (EVA) and 2.3 wt % of paraffin wax and 1.3 wt % of dibutylphthalate (plasticizer) were mixed with 91 wt % of the titanium powder to obtain a mixture.

The mixture was kneaded by a pressure type kneader (kneading machine) under the conditions of a kneading temperature of 100° C. and a kneading time of 60 min to obtain a kneaded product. The kneading was carried out in a nitrogen atmosphere.

Next, the kneaded product was pulverized into pellets with an average particle size of 5 mm. The pellets were put into an injection molding machine, and injected into a mold provided in the machine and having an internal shape corresponding to an external shape of the titanium member to be produced under the molding conditions of a material temperature of 130° C. and an injection pressure of 10.8 MPa (110 kgf/cm$^2$) to obtain a titanium molded body within the mold. At this time, the recess was formed in the titanium molded body. Thereafter, the titanium molded body having the recess was ejected from the mold. This process was repeatedly performed to obtain a specified number of the titanium molded bodies (see FIG. 3A).

Assembling Step

Next, the titanium molded bodies thus obtained and ceramic members produced independently were assembled together to obtain assembled bodies (see FIG. 3B). In this regard, the ceramic molded bodies were composed of zirconia as a major component thereof.

Hereinbelow, description will be made on a method for producing the ceramic members.

Prepared first was zirconia powder with an average particle size of 0.5 μm, which was produced by a co-precipitation method.

A binder composed of 4.8 wt % of polystyrene (PS), 3.8 wt % of ethylene-vinyl acetate copolymer (EVA) and 4.8 wt % of paraffin wax and 2.6 wt % of dibutylphthalate (plasticizer) were mixed with 84 wt % of the zirconia powder to obtain a mixture.

The mixture was kneaded by a pressure type kneader (kneading machine) under the conditions of a kneading temperature of 100° C. and a kneading time of 60 min to obtain a kneaded product. The kneading was carried out in a nitrogen atmosphere.

Next, the kneaded product was pulverized into pellets with an average particle size of 3 mm. The pellets were put into an injection molding machine, and injected into a mold provided in the machine and having an internal shape corresponding to an external shape of the ceramic member to be produced under the molding conditions of a material temperature of 140° C. and an injection pressure of 10.8 MPa (110 kgf/cm$^2$) to obtain a ceramic molded body within the mold. At this time, the protrusion was formed in the ceramic molded body. Thereafter, the ceramic molded body having the protrusion was ejected from the mold. This process was repeatedly performed to obtain a specified number of the ceramic molded bodies.

Next, the ceramic molded bodies thus obtained were degreased under the conditions of a degreasing temperature of 500° C., a degreasing time of two hours and a degreasing atmosphere of nitrogen gas (set to the atmospheric pressure). By doing so, the ceramic molded bodies were transformed into ceramic degreased bodies.

Continuously, the ceramic degreased bodies thus obtained were sintered under the conditions of a sintering temperature of 1450° C., a sintering time of three hours and a sintering atmosphere of air. By doing so, the ceramic degreased bodies were transformed into ceramic members.

Each of the ceramic members obtained in this manner had a protrusion whose cross-sectional shape was non-circular (rectangular). Furthermore, each of the ceramic members had a cross-sectional area increasing portion extending over a full heightwise length of the protrusion.

An angle θ between a surface (circumference surface) of the cross-sectional area increasing portion and a heightwise axis of the protrusion was 1.5°.

Degreasing Step

Next, the assembled bodies thus obtained were degreased under the conditions of a degreasing temperature of 450° C., a degreasing time of one hour and a degreasing atmosphere of nitrogen gas (set to the atmospheric pressure).

By doing so, the binder contained in the titanium molded bodies was removed therefrom to transform them into titanium degreased bodies (see FIG. 3C).

Sintering Step

Next, the assembled bodies were sintered under the conditions of a sintering temperature of 1200° C., a sintering time of three hours and a sintering atmosphere of argon gas (set to the atmospheric pressure).

By doing so, the titanium degreased bodies were transformed into titanium members. Thus, the titanium members were firmly fixed and joined to the ceramic members (see FIG. 3D).

Machining Step

Subsequently, the abutments as desired were obtained by machining the titanium members and adjusting a shape of each of male thread portions thereof. In the abutments thus obtained, the protrusion of each of the ceramic members was fitted to the recess of each of the titanium members so that the titanium members and the ceramic members could be strongly fixed.

Finally, dental implants were obtained by combining the fixtures and the abutments produced as above.

Examples 2 to 7

Dental implants were manufactured in the same manner as in Example 1, except that the composition ratio of the composition (the kneaded product) used in producing the abutments (the titanium members and the ceramic members) was changed, that the same composition as that of the titanium molded bodies was used as the composition (the kneaded product) for production of the fixtures, and that the production conditions of the abutments were changed as shown in Table 1.

Comparative Example 1

Dental implants were manufactured in the same manner as in Example 1, except that each of the abutments was produced in the form of an integral titanium member having the same external shape as that of each of the abutments produced in the foregoing examples.

Hereinbelow, an abutment production method according to this comparative example will be described in detail.

First, a binder composed of 2.7 wt % of polystyrene (PS), 2.7 wt % of ethylene-vinyl acetate copolymer (EVA) and 2.3 wt % of paraffin wax and 1.3 wt % of dibutylphthalate (plasticizer) were mixed with 91 wt % of titanium powder having an average particle size of 20 µm, which was produced by a gas atomizing method, to obtain a mixture.

The mixture was kneaded by a pressure type kneader (kneading machine) under the conditions of a kneading temperature of 100° C. and a kneading time of 60 min to obtain a kneaded product. The kneading was carried out in a nitrogen atmosphere.

Next, the kneaded product was pulverized into pellets with an average particle size of 5 mm. The pellets were put into an injection molding machine, and injected into a mold provided in the machine and having an internal shape corresponding to an external shape of the abutment to be produced under the molding conditions of a material temperature of 130° C. and an injection pressure of 10.8 MPa (110 kgf/cm$^2$) to obtain a molded body within the mold. Thereafter, the molded body was ejected from the mold. This process was repeatedly performed to obtain a specified number of the molded bodies.

In this regard, it is to be noted that at this time, a size of each of the molded bodies was decided by taking into account shrinkage thereof which would occur in the subsequent degreasing and sintering steps.

Next, the molded bodies thus obtained were degreased under the conditions of a degreasing temperature of 450° C., a degreasing time of one hour and a degreasing atmosphere of nitrogen gas (set to the atmospheric pressure). By doing so, the binder contained in the molded bodies was removed therefrom to transform them into degreased bodies.

Then, the degreased bodies were sintered under the conditions of a sintering temperature of 1200° C., a sintering time of three hours and a sintering atmosphere of argon gas (set to the atmospheric pressure) to obtain sintered bodies.

Subsequently, the abutments as desired were obtained by machining the sintered bodies and adjusting a shape of each of male thread portions thereof.

Comparative Example 2

Dental implants were manufactured in the same manner as in Example 1, except that each of the abutments was produced in the form of an integral zirconia member having the same external shape as that of each of the abutments produced in the foregoing examples.

Hereinbelow, an abutment production method according to this comparative example will be described in detail.

First, a binder composed of 4.8 wt % of polystyrene (PS), 3.8 wt % of ethylene-vinyl acetate copolymer (EVA) and 4.8 wt % of paraffin wax and 2.6 wt % of dibutylphthalate (plasticizer) were mixed with 84 wt % of zirconia powder having an average particle size of 0.5 µm, which was produced by a co-precipitation method, to obtain a mixture.

The mixture was kneaded by a pressure type kneader (kneading machine) under the conditions of a kneading temperature of 100° C. and a kneading time of 60 min to obtain a kneaded product. The kneading was carried out in a nitrogen atmosphere.

Next, the kneaded product was pulverized into pellets with an average particle size of 3 mm. The pellets were put into an injection molding machine, and injected into a mold provided in the machine and having an internal shape corresponding to an external shape of the abutment to be produced under the molding conditions of a material temperature of 140° C. and an injection pressure of 10.8 MPa (110 kgf/cm$^2$) to obtain a molded body within the mold. Thereafter, the molded body was ejected from the mold. This process was repeatedly performed to obtain a specified number of the molded bodies.

In this regard, it is to be noted that at this time, a size of each of the molded bodies was decided by taking into account shrinkage which would occur in the subsequent degreasing and sintering steps.

Next, the molded bodies thus obtained were degreased under the conditions of a degreasing temperature of 500° C., a degreasing time of two hours and a degreasing atmosphere of nitrogen gas (set to the atmospheric pressure). By doing so, the binder contained in the molded bodies was removed therefrom to transform them into degreased bodies.

Then, the degreased bodies were sintered under the conditions of a sintering temperature of 1450° C., a sintering time of three hours and a sintering atmosphere of air to obtain sintered bodies.

Subsequently, the abutments as desired were obtained by machining the sintered bodies and adjusting a shape of each of male thread portions thereof.

Comparative Example 3

Dental implants were manufactured in the same manner as in Example 1, except that each of the abutments was produced by independently producing and bonding titanium members (titanium sintered bodies) and ceramic members (ceramic sintered bodies) with dental cement.

In this regard, it is to be noted that each of the abutments had the same external shape as that of each of the abutments produced in the foregoing examples.

Hereinbelow, an abutment production method according to this comparative example will be described in detail.

Production of Titanium Members

First, a binder composed of 2.7 wt % of polystyrene (PS), 2.7 wt % of ethylene-vinyl acetate copolymer (EVA) and 2.3 wt % of paraffin wax and 1.3 wt % of dibutylphthalate (plasticizer) were mixed with 91 wt % of titanium powder having an average particle size of 20 μm, which was produced by a gas atomizing method, to obtain a mixture.

The mixture was kneaded by a pressure type kneader (kneading machine) under the conditions of a kneading temperature of 100° C. and a kneading time of 60 min to obtain a kneaded product. The kneading was carried out in a nitrogen atmosphere.

Figure 5:
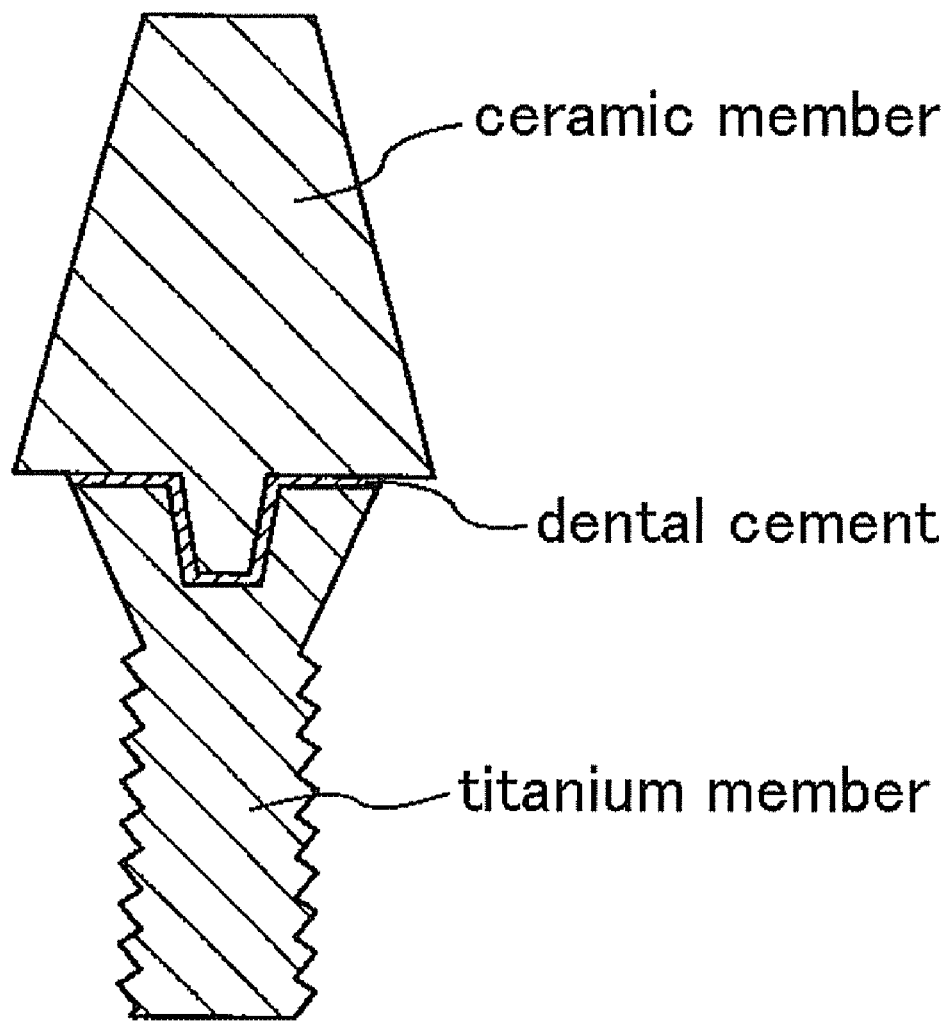
FIG. 5 is a vertical section view showing an abutment manufactured in Comparative Example 3.

Next, the kneaded product was pulverized into pellets with an average particle size of 5 mm. The pellets were put into an injection molding machine, and injected into a mold provided in the machine and having an internal shape corresponding to an external shape of a lower part of an abutment shown in FIG. 5 (a member to be threadedly coupled to the fixture) under the molding conditions of a material temperature of 130° C. and an injection pressure of 10.8 MPa (110 kgf/cm$^2$) to obtain a titanium molded body within the mold. Thereafter, the titanium molded body was ejected from the mold. This process was repeatedly performed to obtain a specified number of the titanium molded bodies.

In this regard, it is to be noted that at this time, a size of each of the titanium molded bodies was decided by taking into account shrinkage which would occur in the subsequent degreasing and sintering steps.

Next, the titanium molded bodies thus obtained were degreased under the conditions of a degreasing temperature of 450° C., a degreasing time of one hour and a degreasing atmosphere of nitrogen gas (set to the atmospheric pressure). By doing so, the binder contained in the titanium molded bodies was removed therefrom to transform them into titanium degreased bodies.

Then, the titanium degreased bodies were sintered under the conditions of a sintering temperature of 1200° C., a sintering time of three hours and a sintering atmosphere of argon gas (set to the atmospheric pressure) to obtain titanium sintered bodies.

Subsequently, the titanium members as desired were obtained by machining the titanium sintered bodies and adjusting a shape of each of male thread portions thereof.

Production of Ceramic Members

First, a binder composed of 4.8 wt % of polystyrene (PS), 3.8 wt % of ethylene-vinyl acetate copolymer (EVA) and 4.8 wt % of paraffin wax and 2.6 wt % of dibutylphthalate (plasticizer) were mixed with 84 wt % of zirconia powder having an average particle size of 0.5 μm, which was produced by a co-precipitation method, to obtain a mixture.

The mixture was kneaded by a pressure type kneader (kneading machine) under the conditions of a kneading temperature of 100° C. and a kneading time of 60 min to obtain a kneaded product. The kneading was carried out in a nitrogen atmosphere.

Next, the kneaded product was pulverized into pellets with an average particle size of 3 mm. The pellets were put into an injection molding machine, and injected into a mold provided in the machine and having an internal shape corresponding to an external shape of an upper part of an abutment shown in FIG. 5 (a member to be capped by a crown restoration) under the molding conditions of a material temperature of 140° C. and an injection pressure of 10.8 MPa (110 kgf/cm$^2$) to obtain a ceramic molded body within the mold. Thereafter, the ceramic molded body was ejected from the mold. This process was repeatedly performed to obtain a specified number of the ceramic molded bodies.

In this regard, it is to be noted that at this time, a size of each of the ceramic molded bodies was decided by taking into account shrinkage which would occur in the subsequent degreasing and sintering steps.

Next, the ceramic molded bodies thus obtained were degreased under the conditions of a degreasing temperature of 500° C., a degreasing time of two hours and a degreasing atmosphere of nitrogen gas (set to the atmospheric pressure). By doing so, the binder contained in the ceramic molded bodies was removed therefrom to transform them into ceramic degreased bodies.

Then, the ceramic degreased bodies were sintered under the conditions of a sintering temperature of 1450° C., a sintering time of three hours and a sintering atmosphere of air to obtain ceramic members.

Bonding of Titanium Members and Ceramic Members (Completion of Abutments)

Subsequently, abutments were produced by bonding the titanium members (the titanium sintered bodies) and the ceramic members (the ceramic sintered bodies) with dental cement ("Glass Ionomer", produced by GC America, Inc.).

The production conditions of the fixtures and the abutments employed in the respective examples and the respective comparative examples are collectively shown in Table 1. The configurations of the dental implants manufactured in the respective examples and the respective comparative examples are collectively shown in Table 2.

Referring to Comparative Example 2 shown in Table 1, the conditions for producing the molded bodies each containing the ceramic powder are indicated in the titanium molded body production step column.

Referring to Comparative Example 3 shown in Table 1, the conditions of the ceramic members bonded to the titanium members with the dental cement are indicated in the assembling step column, the conditions for degreasing the titanium molded body are indicated in the degreasing step column, the conditions for sintering the titanium degreased body are indicated in the sintering step column, and the existence or nonexistence of the machining step is indicated in the machining step column, respectively.

Referring to Comparative Examples 1 and 2 shown in Table 2, the conditions for the portion threadedly coupled to the fixture (the portion corresponding to the titanium member in the present invention) are indicated in the titanium member column, and the conditions for the portion capped by the crown restoration (the portion corresponding to the ceramic member in the present invention) are indicated in the ceramic member column.

TABLE 1

| | Titanium Molded Body Production Step | | | | Assembling Step Ceramic Member Used for Assembling | | | | |
|---|---|---|---|---|---|---|---|---|---|
| | Titanium Molded Body | | | | | | | | Angle θ between Surface of Cross-sectional Area Increasing Portion and Heightwise Axis of Protrusion [°] |
| | Content Percentage of Powder [wt %] | Content Percentage of Binder [wt %] | Material Temperature [° C.] | Injection Pressure [MPa] | Composition | Height of Protrusion [mm] | Cross-sectional Shape of Protrusion | Existence or Non-existence of Cross-sectional Area Increasing Portion | |
| Ex. 1 | 91 | 7.7 | 130 | 10.8 | ZrO$_2$ | 4 | Rectangle | Existence | 1.5 |
| Ex. 2 | 91 | 7.7 | 130 | 10.8 | ZrO$_2$ | 4 | Rectangle | Non-existence | — |
| Ex. 3 | 91 | 7.7 | 130 | 10.8 | ZrO$_2$ | 4 | Ellipsoid | Existence | 1 |
| Ex. 4 | 91 | 7.7 | 130 | 10.8 | ZrO$_2$ | 2 | Ellipsoid | Existence | 4 |
| Ex. 5 | 91 | 7.7 | 130 | 10.8 | ZrO$_2$ | 5 | Rectangle | Existence | 1.5 |
| Ex. 6 | 65 | 29.4 | 130 | 10.8 | ZrO$_2$ | 4 | Rectangle | Existence | 1.5 |
| Ex. 7 | 95 | 4.2 | 130 | 10.8 | ZrO$_2$ | 4 | Rectangle | Existence | 1.5 |
| Com. Ex. 1 | 91 | 7.7 | 130 | 10.8 | — | — | — | — | — |
| Com. Ex. 2 | 84 | 13.4 | 140 | 10.8 | — | — | — | — | — |
| Com. Ex. 3 | 91 | 7.7 | 130 | 10.8 | ZrO$_2$ | 4 | Ellipsoid | Non-existence | — |

| | Degreasing Step | | | Sintering Step | | | Machining Step Existence or Non-existence of This Step |
|---|---|---|---|---|---|---|---|
| | Processing Temperature [° C.] | Processing Time [hours] | Atmosphere | Processing Temperature [° C.] | Processing Time [hours] | Atmosphere | |
| Ex. 1 | 450 | 1 | N$_2$ | 1200 | 3 | Ar | Existence |
| Ex. 2 | 450 | 1 | N$_2$ | 1200 | 3 | Ar | Existence |
| Ex. 3 | 450 | 1 | N$_2$ | 1200 | 3 | Vacuum | Existence |
| Ex. 4 | 450 | 1 | N$_2$ | 1200 | 3 | Vacuum | Existence |
| Ex. 5 | 450 | 1 | N$_2$ | 1200 | 3 | Vacuum | Existence |
| Ex. 6 | 450 | 3 | N$_2$ | 1200 | 3 | Ar | Existence |
| Ex. 7 | 450 | 1 | N$_2$ | 1200 | 3 | Ar | Existence |
| Com. Ex. 1 | 450 | 1 | N$_2$ | 1200 | 3 | Ar | Existence |
| Com. Ex. 2 | 500 | 2 | N$_2$ | 1450 | 3 | Air | Existence |
| Com. Ex. 3 | 450 | 1 | N$_2$ | 1200 | 3 | Ar | Existence |

TABLE 2

| | Configuration of Abutment | | | | | | | Configuration of Fixture | |
|---|---|---|---|---|---|---|---|---|---|
| | Titanium Member | | Ceramic Member | | | | | | |
| | Constituent Material | Depth of Recess [mm] | Constituent Material | Height of Protrusion [mm] | Existence or Non-existence of Cross-sectional Area Increasing Portion | Angle θ between Surface of Cross-sectional Area Increasing Portion and Heightwise Axis of Protrusion [°] | | Constituent Material | Existence or Non-existence of Cutout Portion |
| Ex. 1 | Ti | 4.2 | ZrO$_2$ | 4 | Existence | 1.5 | | Ti | Existence |
| Ex. 2 | Ti | 4.2 | ZrO$_2$ | 4 | Non-existence | — | | Ti | Existence |
| Ex. 3 | Ti | 4.2 | ZrO$_2$ | 4 | Existence | 1 | | Ti | Existence |
| Ex. 4 | Ti | 2.1 | ZrO$_2$ | 2 | Existence | 4 | | Ti | Existence |
| Ex. 5 | Ti | 5.2 | ZrO$_2$ | 5 | Existence | 1.5 | | Ti | Existence |
| Ex. 6 | Ti | 4.2 | ZrO$_2$ | 4 | Existence | 1.5 | | Ti | Existence |
| Ex. 7 | Ti | 4.2 | ZrO$_2$ | 4 | Existence | 1.5 | | Ti | Existence |
| Com. Ex. 1 | Ti | — | Ti | — | — | — | | Ti | Existence |

TABLE 2-continued

| | Configuration of Abutment | | | | | | | |
|---|---|---|---|---|---|---|---|---|
| | Titanium Member | | Ceramic Member | | | | Configuration of Fixture | |
| | Constituent Material | Depth of Recess [mm] | Constituent Material | Height of Protrusion [mm] | Existence or Non-existence of Cross-sectional Area Increasing Portion | Angle θ between Surface of Cross-sectional Area Increasing Portion and Heightwise Axis of Protrusion [°] | Constituent Material | Existence or Non-existence of Cutout Portion |
| Com. Ex. 2 | ZrO$_2$ | — | ZrO$_2$ | — | — | — | Ti | Existence |
| Com. Ex. 3 | Ti | 4.2 | ZrO$_2$ | 4 | Non-existence | — | Ti | Existence |

2. Bonding of Crown Restoration

In a state that the fixture and the abutment of the dental implant obtained in each of the examples had been threadedly coupled together, a crown restoration was bonded by dental cement ("Superbond", produced by Sun Medical Ltd.) to a surface (a metal bonding surface shown in FIGS. 1A to 1C) of the abutment opposite to a side on which the abutment was threadedly coupled to the fixture.

The crown restoration used was of a type including a metal layer made of gold and arranged on an inner surface side (a surface facing the abutment) and a ceramic portion made of silicon oxide (silica) and aluminum oxide (alumina) and arranged on an outer surface side (a surface opposite to the abutment). Thereafter, the crown restoration was fixed to the dental implant by hardening the dental cement.

With respect to the dental implant obtained in each of the comparative examples, a crown restoration was bonded by dental cement ("Superbond", produced by Sun Medical Ltd.) to a portion corresponding to the metal bonding surface of the abutment obtained in each of the examples. Then, the dental cement was hardened.

3. Evaluation 3-1. Measurement of Elution Amount of Metal Ions

In respect of each of the dental implants of the examples and the comparative examples to which the crown restorations were bonded in the above manner, an elution amount of metal ions was found by the following method.

The abutments to which the crown restorations were bonded were immersed in 80 mL of 1 wt % latic acid solution for three months. Thereafter, the elution amount of titanium in the solution was analyzed by a plasma emission spectroscopy device.

3-2. Measurement of Fixing Strength

In respect of each of the dental implants of the examples and the comparative examples to which the crown restorations were bonded in the above manner (which dental implants were different from the dental implants used in Section 3-1 for measuring the elution amount of metal ions), fixing strength (bonding strength) between the titanium member and the ceramic member was found in the following method.

Figure 6:
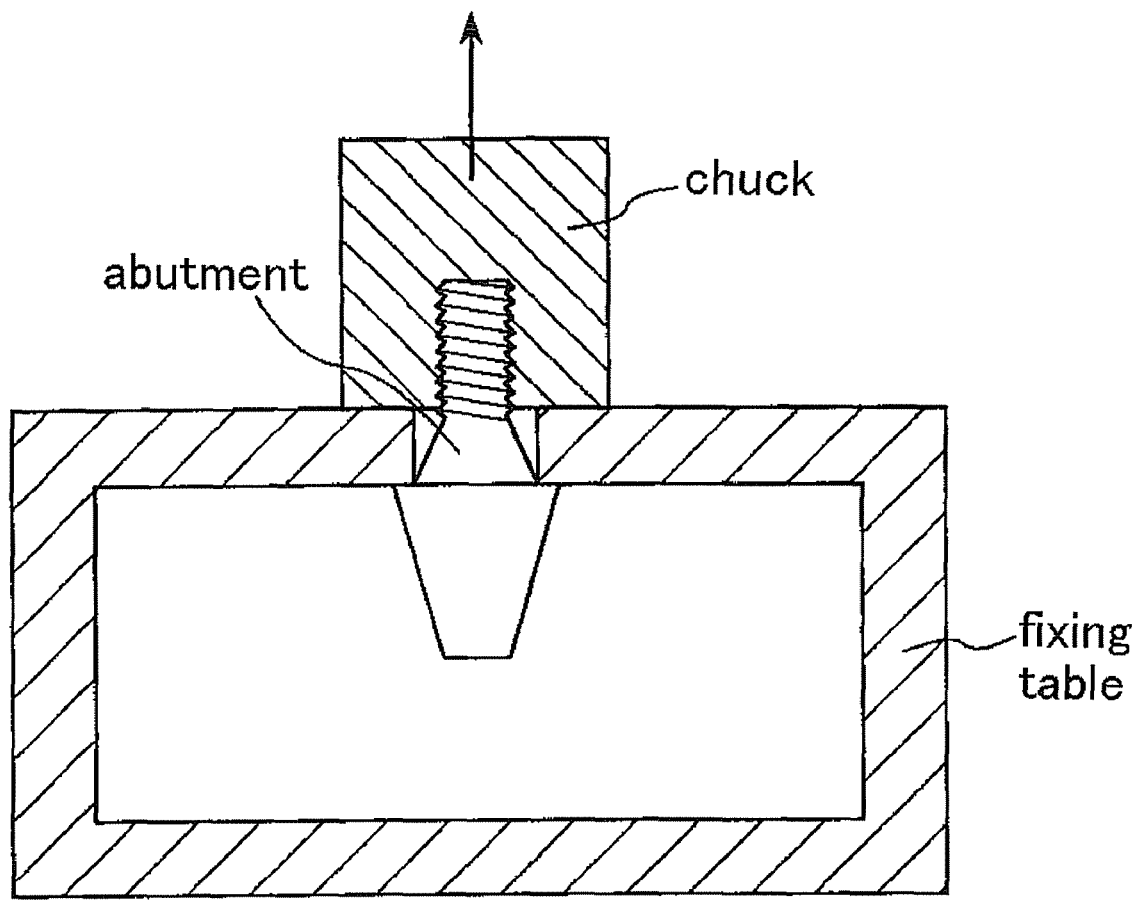
FIG. 6 is a view schematically illustrating a configuration of a jig used in measuring fixing strength and also explaining a method of measuring the fixing strength.

Using a jig as shown in FIG. 6, the abutment was attached to a fixing table and a chuck was mounted to the male thread portion of the abutment. Then, the chuck was mounted to a tensile tester and a strength test was conducted by a drawing method.

3-3. Drop Test

In respect of each of the dental implants of the examples and the comparative examples to which the crown restorations were bonded in the above manner (which dental implants were different from the dental implants used in measuring the elution amount of metal ions in Section 3-1 and the dental implants used in measuring the fixing strength in Section 3-2), a drop test was carried out in the following method.

The dental implants of the examples and the comparative examples to which the crown restorations were bonded (ten dental implants of the examples and ten dental implants of the comparative examples) were dropped one hundred times from a 2 m-high position onto a 2 cm-thick stainless steel plate.

External appearance of each of the dental implants thus dropped was visually observed and evaluated according to the following four criteria.

A: Cracks or defects were not recognized at all in the dental implants.

B: Tiny cracks or defects were recognized in one to five dental implants.

C: Noticeable cracks or defects were recognized in one to five dental implants, or tiny cracks or defects were recognized in six to ten dental implants.

D: Noticeable cracks or defects were recognized in six to ten dental implants.

Results of these evaluations were collectively shown in Table 3.

TABLE 3

| | Elution Amount of Metal Ions [ppm] | Fixing Strength [MPa] | Drop Test |
|---|---|---|---|
| Ex. 1 | 0.6 | 24 | A |
| Ex. 2 | 0.7 | 21 | A |
| Ex. 3 | 0.7 | 22 | A |
| Ex. 4 | 0.6 | 24 | A |
| Ex. 5 | 0.6 | 23 | A |
| Ex. 6 | 0.7 | 23 | A |
| Ex. 7 | 0.8 | 22 | A |
| Com. Ex. 1 | 12 | — | A |
| Com. Ex. 2 | 0 | — | D |
| Com. Ex. 3 | 0.7 | 11 | D |

As is apparent in Table 3, the dental implants of the present invention were all sufficiently low in the elution amount of metal ions. Furthermore, in the dental implants of the present invention, the fixing strength (joint strength) between the titanium members and the ceramic members was superior.

Moreover, the dental implants of the present invention exhibited no mismatching between themselves and the crown restorations, and no mismatching between the titanium members and the ceramic members.

In contrast, no satisfactory result was obtained in the comparative examples. More specifically, the elution amount of metal ions was exceptionally high in Comparative Example 1 in which the abutment was composed of titanium alone.

Furthermore, the mechanical strength of the thread portion was low and the evaluation results of drop test were quite unsatisfactory in Comparative Example 2 in which the abutment was composed of ceramic (zirconia) alone. Moreover, in case of Comparative Example 2, there was a problem in that the thread coupling between the fixture and the abutment was highly likely to be loosened.

Additionally, in case of Comparative Example 3 in which the titanium member and the ceramic member of the abutment were merely bonded by the dental cement, the bonding strength between the titanium member and the ceramic member was not sufficiently great.

Therefore, the titanium member and the ceramic member were separated from each other by a relatively weak force. Furthermore, in case of Comparative Example 3, the mechanical strength was low and the evaluation results of the drop test were quite unsatisfactory.

Further, in respect of Comparative Example 1, a quantity of the dental cement used in bonding the dental implant (the abutment) and the crown restoration was increased so that the dental implant and the crown restoration should not make direct contact with each other.

Then, the same evaluation as noted above was conducted. The results of the evaluation revealed that the bonding strength between the dental implant and the crown restoration was sharply reduced (to 9 MPa).

Furthermore, if the quantity of dental cement was increased as mentioned above, it became quite difficult, when bonding the crown restoration to the abutment, to adjust a height and angle of the crown restoration fixed to the dental implant in conformity with the design.

What is claimed is:

1. A dental implant including an abutment and a fixture to be coupled to the abutment and anchored to a jawbone, and the fixture having a female thread portion,
   wherein the abutment comprises a titanium member composed of a sintered body made from titanium or titanium alloy and having a recess and a male thread portion which makes thread coupling with the female thread portion of the fixture, and a ceramic member composed of oxide-based ceramic and having a protrusion fitted within the recess,
   wherein the protrusion has a heightwise axis and a cross-sectional area increasing portion whose cross-sectional area continuously increases from a base end of the protrusion toward a dead-end portion of the recess, and the cross-sectional area increasing portion has a surface, wherein an angle between the surface of the cross-sectional area increasing portion and the heightwise axis of the protrusion is in a range of 0.3 to 5°,
   wherein a cross-sectional shape of the protrusion is an elliptical shape, wherein the titanium member and the ceramic member are firmly fixed and joined together through an engagement between the recess and the protrusion, and wherein said engagement is obtained due to contraction of a non-sintered body of the titanium member through a sintering process.

2. The dental implant as claimed in claim 1, wherein the ceramic member has a contact surface with which a metal member having a composition different from a constituent material of the titanium member makes contact, and
   wherein the abutment is configured so that a crown having the metal member is fixed to the ceramic member, and the contact surface of the ceramic member is configured to prevent the metal member of the crown from being in contact with the titanium member.

3. The dental implant as claimed in claim 2, wherein the contact surface is tapered toward an opposite direction with respect to the titanium member, and a maximum diameter of the ceramic member is larger than a maximum diameter of the titanium member.

4. A dental implant including an abutment used so as to fix a crown to the abutment and a fixture to be coupled to the abutment and anchored to a jawbone, and the fixture having a female thread portion, wherein the abutment includes a titanium member composed of a sintered body made from titanium or titanium alloy and having a recess and a male thread portion which makes thread coupling with the female thread portion of the fixture, and a ceramic member composed of oxide-based ceramic and having a protrusion fitted within the recess and a contact surface provided opposite the protrusion, and wherein the crown includes a metal portion constituted of a metal composition different from a constituent material of the titanium member, and the metal portion is configured to be in contact with the contact surface,
   wherein the protrusion has a portion whose cross-sectional area continuously increases from a base end of the protrusion toward a dead-end portion of the recess, and a cross-sectional shape of the protrusion is an elliptical shape, wherein the titanium member and the ceramic member are firmly fixed and joined together through an engagement between the recess and the protrusion, wherein said engagement is obtained due to contraction of a non-sintered body of the titanium member through a sintering process, and
   wherein after the crown is fixed to the ceramic member, the contact surface of the ceramic member is configured to prevent the metal portion of the crown from being in contact with the titanium member.

5. The dental implant as claimed in claim 4, wherein the protrusion has a heightwise axis and the portion of the protrusion has a surface, wherein an angle between the surface of the portion and the heightwise axis of the protrusion is in the range of 0.3 to 5°.

6. The dental implant as claimed in claim 4, wherein the contact surface is tapered toward an opposite direction with respect to the titanium member, and a maximum diameter of the ceramic member is larger than a maximum diameter of the titanium member.

* * * * *